(12) United States Patent
Khachaturov et al.

(10) Patent No.: US 9,429,514 B2
(45) Date of Patent: Aug. 30, 2016

(54) OPTICAL INTEGRITY DETECTION SYSTEM

(71) Applicant: LUMENIS LTD., Yokneam Ilit (IL)

(72) Inventors: Arkady Khachaturov, Haifa (IL); Assaf Preiss, Shimshit (IL); Tal Waisman, Haifa (IL); Haim Epshtein, Benyamina (IL)

(73) Assignee: LUMENIS LTD., Yokneam Ilit (IL)

( * ) Notice: Subject to any disclaimer, the term of this patent is extended or adjusted under 35 U.S.C. 154(b) by 0 days.

(21) Appl. No.: 14/851,219

(22) Filed: Sep. 11, 2015

(65) Prior Publication Data

US 2016/0076994 A1 Mar. 17, 2016

Related U.S. Application Data

(60) Provisional application No. 62/050,141, filed on Sep. 14, 2014.

(51) Int. Cl.
| | |
|---|---|
| G01J 4/00 | (2006.01) |
| G01N 21/21 | (2006.01) |
| G01J 1/04 | (2006.01) |
| G01N 21/958 | (2006.01) |
| G01N 21/47 | (2006.01) |

(52) U.S. Cl.
CPC ............ G01N 21/21 (2013.01); G01J 1/0414 (2013.01); G01J 1/0429 (2013.01); G01N 21/958 (2013.01); *G01N 2021/4709* (2013.01)

(58) Field of Classification Search
CPC ......... G01J 4/00; G01J 1/0414; G01J 1/0429
USPC ........................................................ 356/364
See application file for complete search history.

(56) References Cited

U.S. PATENT DOCUMENTS

| | | | | |
|---|---|---|---|---|
| 5,073,025 A | * | 12/1991 | Brooks | G01J 4/00 356/364 |
| 6,850,326 B2 | * | 2/2005 | Thoma | G01J 9/00 356/364 |

* cited by examiner

*Primary Examiner* — Roy M Punnoose
(74) *Attorney, Agent, or Firm* — ISUS Intellectual Property PLL

(57) ABSTRACT

Apparatus is described for determining the optical quality of an optical element, the optical element having proximal and distal end portions. The apparatus also includes at least one non-polarizing beam splitter; at least one polarizing beam splitter; at least a first detector operatively associated with the at least one non-polarizing beam splitter; at least a second detector operatively associated with the at least one polarizing beam splitter. The apparatus includes a mechanism to transmit at least one beam of coherent light energy through the at least one non-polarizing beam splitter and through the at least one polarizing beam splitter, the beam being directed to the proximal and distal end portions of the optical element; the beam of coherent light energy that is reflected from the proximal end portion of the optical element is directed back through the at least one polarizing and the at least one non-polarizing beam splitters to the first detector; the beam that is reflected from the distal end portion of the optical element is directed back through the at least one polarized beam splitter to the second detector; and, the energy level detected by the first and the second detectors provides a measure of optical quality of the optical element.

18 Claims, 2 Drawing Sheets

OPTICAL INTEGRITY DETECTION SYSTEM

RELATED APPLICATIONS

This application is related to and claims priority to U.S. Provisional Application Ser. No. 62/050,141, filed Sep. 14, 2014, the entirety of which is herein incorporated by reference.

BACKGROUND OF THE PRESENT INVENTION

Laser systems usually include a laser generator, a delivery system and a laser console which contains the device or devices to control the operation of the laser and delivery system. Such delivery systems may include, for example, a light guide, an articulated arm or an optical fiber. Light exiting the delivery system may be directed to target a tissue to be treated. Different factors influence the efficiency of the laser treatment. The console typically also includes a programmable controller which may include hardware and programmable software, suitable processors and memory for storage of data and program instructions.

Among these factors are internal factors which characterize the laser generator such as wavelength, pulse duration and power. In addition, factors which are external to the laser cavity may also influence the efficiency of the treatment. Among these external factors are the characteristic of the target tissue, the distance between the distal end of the laser delivery system and the target tissue and the integrity of the delivery system. The last two factors are the subject of US patent publications US2013123769 and US2013235369 respectively, commonly assigned to the assignee of the present application, incorporated by reference herein in their entireties.

It is one aspect of the present invention to provide a system and method to detect and monitor the optical connection between a laser generator and a light delivery system which may also influence the efficiency of the laser treatment as well as addressing any safety issues which may be present.

SUMMARY OF THE PRESENT INVENTION

In an aspect, a method for determining the optical quality of an optical element is disclosed; the optical element has proximal and distal end portions and includes: at least one non-polarizing beam splitter; at least one polarizing beam splitter; at least a first detector operatively associated with the at least one non-polarizing beam splitter; and at least a second detector operatively associated with the at least one polarizing beam splitter; and the method includes: transmitting at least one beam of coherent light energy through the at least one non-polarizing beam splitter and through the at least one polarizing beam splitter; the beam being directed to the proximal and distal end portions of the optical element; the beam of coherent light energy reflected from the proximal end portion of the optical element being directed back through the at least one polarizing and the at least one non-polarizing beam splitters to the first detector; the beam reflected from the distal end portion of the optical element being directed back through the at least one polarized beam splitter to the second detector; and wherein the energy level detected by the first and the second detectors provides a measure of optical quality of the optical element. A device or apparatus, including a digital memory associated with the laser console, may be provided to store the readings detected by the detectors disclosed.

In another aspect, the beam reflected back from the proximal end portion of the optical element is P-polarized and the beam reflected back from the distal end portion of the optical element is at least partially S-polarized. . The beam reflected back from the proximal end portion of the optical element is that of the polarization state that corresponds to the full transmission axis of the polarizing beam splitter.

In yet another aspect, the method further includes the step of providing a calibration medium, in which the calibration medium is placed or mounted on the distal end portion of the optical element.

In another aspect, the method further includes the step of storing the energy level detected by one or more of the first and second detectors.

In yet a further aspect, a third detector may be included, the third detector being operatively associated with the at least one non-polarizing beam splitter and positioned to receive a portion of the beam of coherent light energy to provide a normalization factor measurement.

In an aspect, the at least one non-polarizing beam splitter and the polarizing beam splitter are arranged in a tandem manner and the beam of coherent light energy passed first through the non-polarizing beam splitter and then the polarizing beam splitter before being transmitted to the optical element. Further, a mirror may be positioned after the polarizing beam splitter to fold the light path of the coherent light beam towards the proximal end portion of the optical element. Yet further, a light filter element may be interposed between the polarized beam splitter and the mirror.

In yet a further aspect, an apparatus is disclosed for determining the optical quality of an optical element, the optical element having proximal and distal end portions. The apparatus includes at least one non-polarizing beam splitter; at least one polarizing beam splitter; at least a first detector operatively associated with the at least one non-polarizing beam splitter; at least a second detector operatively associated with the at least one polarizing beam splitter.

In another aspect, the apparatus may include a mechanism to transmit at least one beam of coherent light energy through the at least one non-polarizing beam splitter and through the at least one polarizing beam splitter, the beam being directed to the proximal and distal end portions of the optical element. The beam of coherent light energy that is reflected from the proximal end portion of the optical element is directed back through the at least one polarizing and the at least one non-polarizing beam splitters to the first detector; the beam that is reflected from the distal end portion of the optical element is directed back through the at least one polarized beam splitter to the second detector; and, the energy level detected by the first and the second detectors provides a measure of optical quality of the optical element.

DETAILED DESCRIPTION OF THE PRESENT INVENTION

Figure 1:
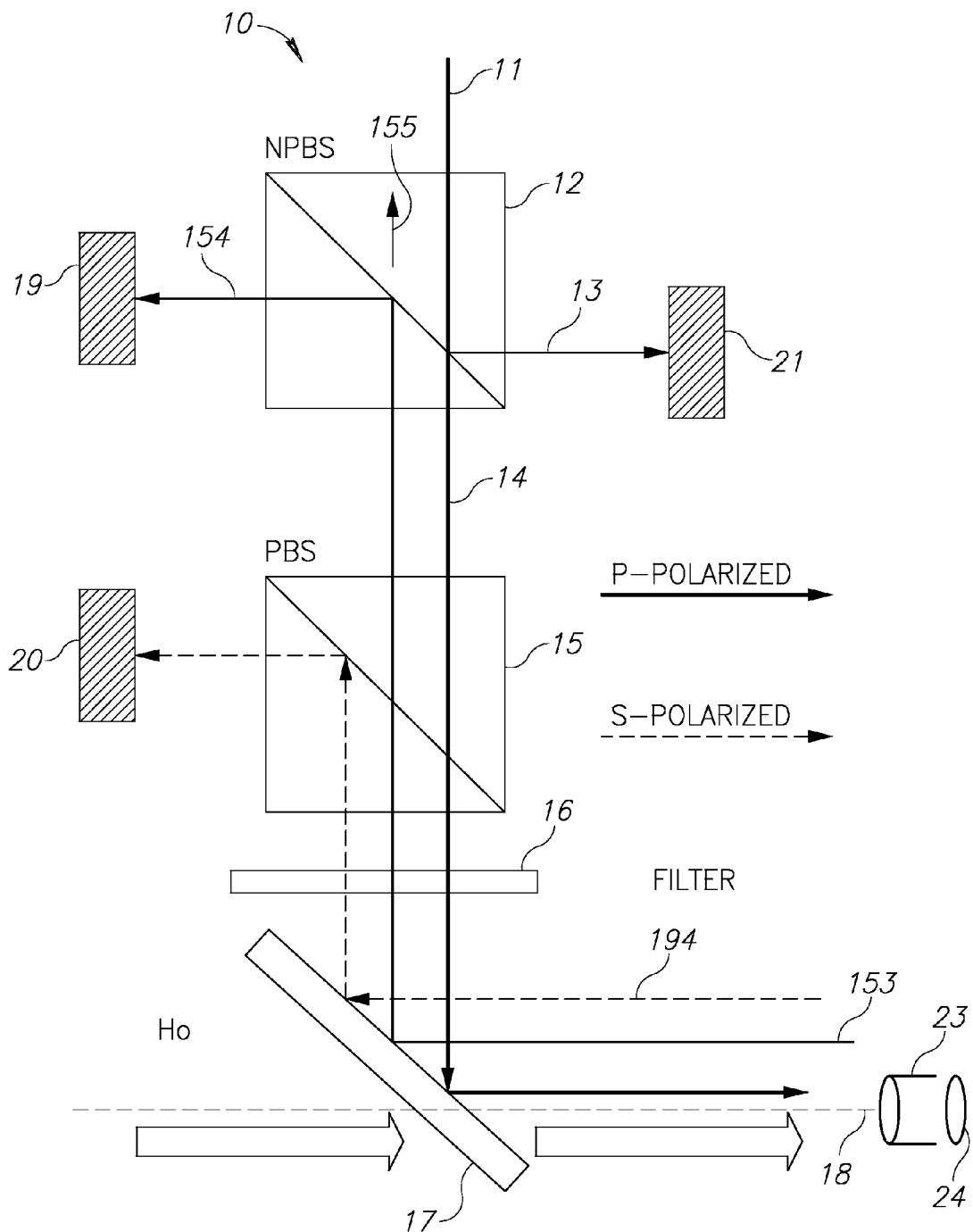
FIG. 1 illustrates an embodiment of the present invention.

FIG. 1 shows one embodiment 10 of the present invention. Aiming beam 11 exits a laser source such as a diode laser (not shown) and enters a glass crystal Non-Polarizing Beam Splitter (NPBS) 12. As a coherent monochromatic light source, such a laser diode generates a polarized aiming beam. The polarized aiming laser beam is split by NPBS 12 into sub-beams 13 and 14. NPBS 12 splits a beam entering the glass crystal by a certain ratio regardless of its polarization. A glass crystal may be designed to split a beam in a way in which most of a beam, like beam 11, goes through the crystal e.g. 95% and a smaller portion of the beam e.g. 5% is split out at a 90 degree angle. Beam 13 is directed to detector 21 which may be used for normalization purposes as known to those skilled in the art.

It is to be understood that the readings or signals detected by the detector 21, or, for that matter, detectors 19 or 20 may be stored in a laser console, known in the art, which controls the operation of the laser device disclosed herein as well as the optical integrity detection systems and methods disclosed in the present application. In addition, the laser console may include a controller of a known type, the controller including hardware and software programming suitable for controlling the operation of the laser device as well as the optical integrity detection system of the present invention. For example, when in the calibration mode, readings data from one or more of the three detectors 19, 20 and 21 may be stored and a date assigned to that stored data. That stored data may later be compared to later in time calibration results to give an indication of the optical integrity of the system over time.

Beam 14 retains its original polarization and therefore continues and passes through a Polarizing Beam Splitter (PBS) 15 which is configured to pass the aiming beam's original polarization as it entered the beam splitter 15. Beam 14 continues on through filter 16 to a beam combiner 17 made of a selective mirror and is injected along the main treatment laser optical axis 18 which targets a fiber port 23. The fiber port 23 connects a laser delivery system such as an optical fiber to the main optical axis of the system. Thus, the treatment laser and aiming laser beam propagate in a free air medium within the main laser console (not shown but well known to those skilled in the art) through different optical elements until reaching the fiber port. In the fiber port 23, a lens 24 focuses the laser beams into a delivery system 119 (shown in FIG. 2, discussed below) such as an optical fiber, a wave guide or an articulated aim. The optical coupling quality across the fiber port affects, among other things, the quality of the laser beams reaching the target tissue and the effectiveness of the laser treatment. It is one aspect of the present invention to measure and monitor the quality of the optical coupling across this optical connector.

Figure 2:
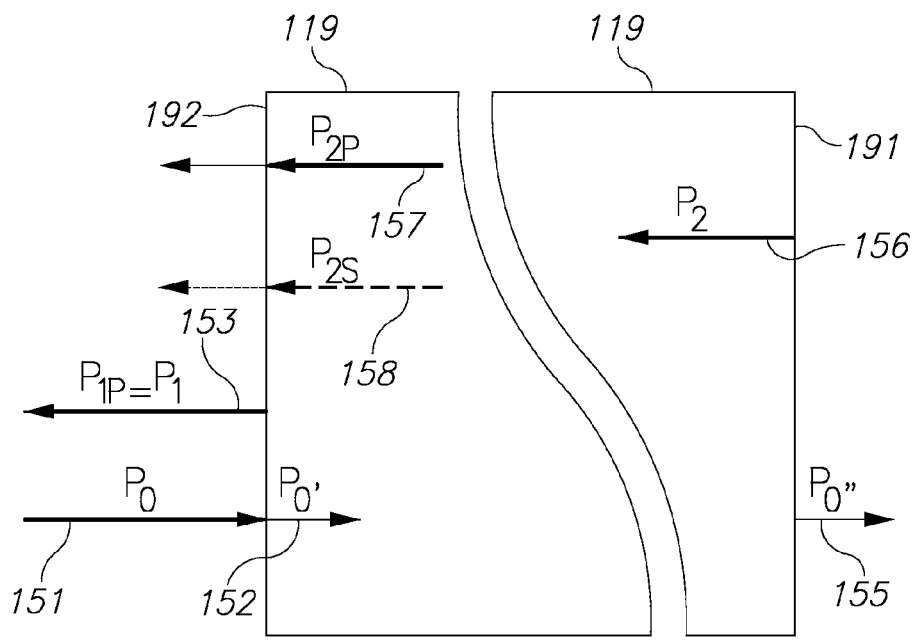
FIG. 2 illustrates one embodiment of a delivery system.
Figure 3:
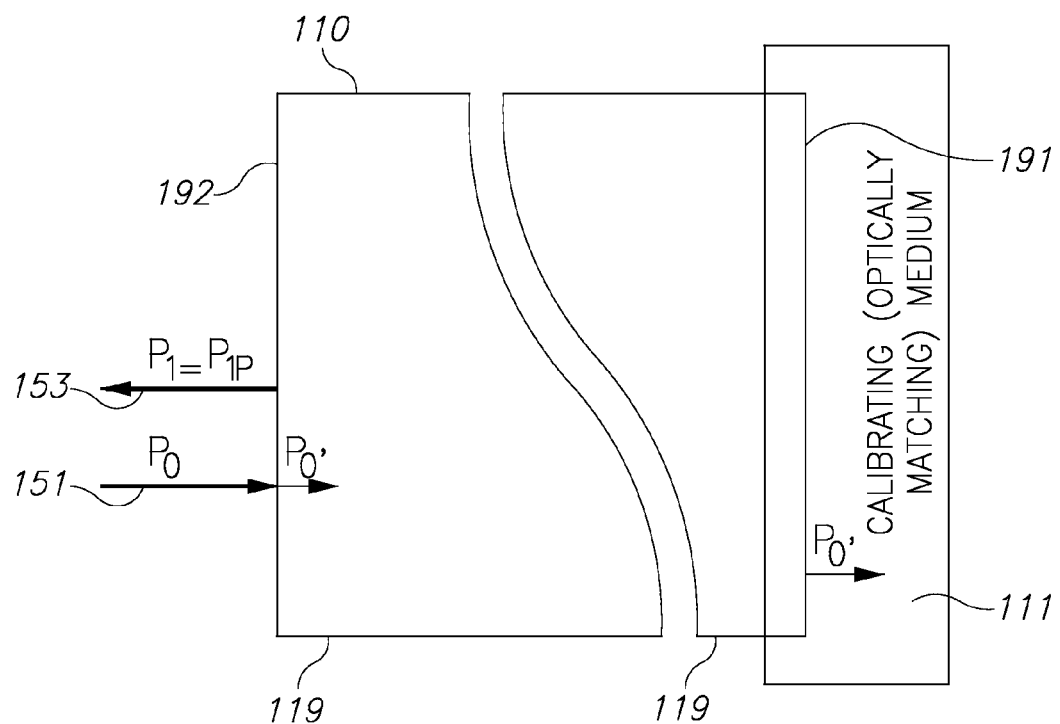
FIG. 3 illustrates the delivery system of FIG. 2 with an optical calibration medium.

According to another aspect of the present invention, an optical calibration unit 110 having an optical calibration media 111 into which the distal end of the laser delivery system 119 may be injected is described in FIG. 3. Calibration media 111 is characterized by having the same refraction index as of the laser delivery system 119. During this calibration process, which may be done prior to the laser treatment, a calibration system 111 is connected to the distal end of the laser delivery system 119 and the aiming beam 11 (from FIG. 1) is turned on. The aiming beam 11 propagates as described above and as shown in FIG. 1 from its origin through NPBS 12, then to PBS 15, to folding mirror 17 and through the main optical axis of the laser system 18 until it reaches laser delivery system 119 as beam 151 portion $P_O$ (see FIGS. 2 and 3).

A first portion of beam 151($P_O$), beam 152 ($P_{O'}$), continues into the laser delivery system 119 and reaches calibration media 111 through distal portion 191. Due to refractive index matching between the laser delivery system 119 and calibration media 111 there is no optical back reflection from distal end 191 of laser delivery system 119 and beam portion 152 ($P_{O'}$) which entered through proximal end 192 exits through distal end 191. However, the proximal end 192 of laser delivery system 119 does create some reflection so that an impinging beam 152 ($P_O$) creates a backscattered beam 153 ($P_1$). The intensity of such a backscattered beam 153 ($P_1$) is a function, among other things, of the power and alignment of the impinging beam 151 ($P_O$), the optical quality of surface 192 and optical alignment of the laser delivery system 119 versus the main optical axis of 18 of the laser system. The polarization of aiming beam 11 is kept unchanged along the propagation path described above and likewise the polarization of the back reflected beam 153 ($P_1$). The notation of beam 153 ($P_{1P}$) as shown in FIG. 3 is used as an example to show that, assuming the original aiming laser beam 11 has a P polarization, then back reflected beam 153 ($P_1$) has the same polarization, denoted in FIGS. 2 and 3 as $P_{1P}$.

Returning now to FIG. 1, and assuming the system remains in a calibration mode, back reflected beam 153 impinges selective mirror 17 which is opaque and configured to fold aiming beam's wavelength, and continues through PBS 15 to NPBS 12. Due to a polarization matching, PBS 15 is transparent to the beam 153. However, NPBS 12 splits beam 153 so that a portion of the beam 154 is directed to detector 191 and a portion of the beam 155 goes through the crystal 12. Knowing the ratio of such split (which is a pre-established characteristic of the crystal 12) and by measuring the intensity of the beam 154 on detector 191, one may calculate the total power P1 which is reflected from proximal end 192 of laser delivery system 119 at the time of calibration. This measured value characterizes the state of the entire system before the treatment starts and before the high power treatment laser starts and may be stored in the main laser system for future use as will be described below.

Turning now to FIG. 2, this figure shows laser delivery system 119 during operation without the calibration system 110 of FIG. 3. As can be seen, aiming beam 151 ($P_O$) impinges on the proximal end 192 of laser delivery system 119. A portion 153 ($P_{1P}$) is back reflected while another portion 152 ($P_{O'}$) goes into the laser delivery system 119. Beam portion 152 ($P_{O'}$) propagates along the laser delivery system. Such a laser delivery system may be long, curved and perhaps even rotated. As a result, the polarity of propagating beam portion 152 ($P_{O'}$) may change. Once the beam portion 152 impinges on the distal end 191 of laser delivery system 119, one portion of propagating beam portion 152 ($P_{O'}$) will exit the laser delivery system as beam 155 ($P_{O''}$) targeting a target tissue while a second portion, beam 156,($P_2$,) will be back reflected and will propagate upstream along laser delivery system 119.

Back reflected aiming beam portion 156 ($P_2$) consists of two orthogonal polarization components P and S. As shown in FIG. 2, beams 157 and 158, ($P_{2P}$ and $P_{2S}$) are schematic presentations of these two components. During operation, back reflected aiming beam portions 153, 157 and 158 ($P_{1P}$, $P_{2P}$ and $P_{2S}$) are illustrated as beam portions 153 and 194 in FIG. 1. P polarization components are represented by a solid line 153 in FIG. 1 and the S polarization components represented by a dashed line 194, also illustrated in FIG. 1.

As mentioned above, during calibration, P polarized beam portion 153 is originated only by proximal surface 192 and there is no S polarized beam component 194. However, during operation, P polarized beam portion 153 consists of the sum of P polarized beam portion 153 ($P_{1P}$) reflected from the proximal end 192 and the P polarized beam portion 157 ($P_{2P}$) reflected from the distal end 191. In addition, due to polarization shifts of beam portions propagating through and along laser delivery system 119, an S polarized beam portion 194 is created. Beam portions 153 and 194 are folded by selective mirror 17, as seen in FIG. 1, from the main optical axis 18 toward the optical assembly which consists of NPBS 12 and PBS 15 and detectors 19 and 20. Following the P polarized beam portion 153, selective mirror 17 folds beam portion 153 toward PBS 15. PBS 15 is transparent to P polarization and therefore beam portion 153 goes through PBS 15 and reaches NPBS 12. NPBS 12 splits beam 153 into a first portion 154 which hits detector 19 and a second portion 155 which goes though the crystal 12. Measuring and monitoring the power of beam portion 154 hitting detector 19 may give an indication of changes to the optical coupling quality at the fiber port. A decreased quality of the optical coupling at fiber port or any degradation in the optical quality of surface 192 may result in increasing power of beam portion 154.

S polarized beam portion 194 impinges PBS 15 which acts as a folding mirror to this aiming beam portion and directs it toward detector 20. Since S polarized beam portion originated from the distal surface 191 of laser delivery system 119, monitoring changes in the power of such signal may indicate degradation of the optical quality of surface 191. Since laser delivery systems such as an optical fiber or a waveguide are characterized by a longitudinal symmetry, the ratio between beam portions 157 ($P_{2P}$) and 158 ($P_{2S}$) is about 1. Moreover, signal strength of beam 157 ($P_{2P}$) is much smaller than that of beam 158 ($P_{1P}$). This is due to the fact, among other things, that beam portion 158 ($P_{1P}$) is originated by surface 192 in which air having a refraction index of 1 meets an optical fiber core material which has a refractive index of about 1.5, while beam portion 157 ($P_{2P}$) is originated at surface 191 in which the same fiber meets a saline solution environment which has a refractive index of an about 1.4. Therefore, according to one aspect of the present invention, monitoring power changes on detector 19 bigger than about 5% may indicate problems in the fiber port while changes below about 5% may also occur due to some optical degradation on the distal surface 191. In order to analyze the relative contributions of surfaces 191 and 192 while measuring changes smaller than about 5%, the value as measured on detector 20 may help evaluating beam portion 157 ($P_{2P}$) assuming it has a similar magnitude to beam portion 158($P_{2S}$).

Filter 16 may be used to filter out light different than the aiming beam light in order to avoid artifacts and for the purpose of receiving a better signal. However, according to another aspect of the present invention, a laser delivery system 119 may be used through a working channel of an endoscope or a laparoscope. Often, during surgery, a visualization system is used. In order to improve visibility, a light source may deliver white or other light into the working area. It is another aspect of the present invention to also measure and monitor the intensity of such light. Different filters 16 may be used in connection with different aspects of the invention to block or to pass different wavelengths of light. For example, if the filter is configured to pass light which is designed to illuminate the working area, then a measurement resulting in the detection of no light in an appropriate detector may indicate that distal end 191 of the laser delivery system 119 has not yet reached the end of the scope and therefore any activation of the treatment laser may damage the expensive scope or surrounding tissue should the laser beam breach and penetrate the scope wall. Therefore, as a safety mechanism, such an indication may be used to cause the laser to be disabled to make sure there is no potential damage. As another example, during the interaction between the treatment laser and the target tissue, a plasma may be created. Such a plasma is a source of optical energy. Having an appropriate filter 16 which is configured to pass wavelengths characterized by such a plasma may provide indication of the intensity and efficacy of the laser/tissue interaction.

What we claim is:

1. A method for determining the optical quality of an optical element, the optical element having proximal and distal end portions, comprising:
    providing at least one non-polarizing beam splitter;
    providing at least one polarizing beam splitter;
    providing at least a first detector operatively associated with the at least one non-polarizing beam splitter;
    providing at least a second detector operatively associated with the at least one polarizing beam splitter;
    the method comprising:
    transmitting at least one beam of coherent light energy through the at least one non-polarizing beam splitter and through the at least one polarizing beam splitter, the beam being directed to the proximal and distal end portions of the optical element;
    the beam of coherent light energy reflected from the proximal end portion of the optical element being directed back through the at least one polarizing and the at least one non-polarizing beam splitters to the first detector;
    the beam reflected from the distal end portion of the optical element being directed back through the at least one polarized beam splitter to the second detector;
    wherein the energy level detected by the first and the second detectors provides a measure of optical quality of the optical element.

2. The method of claim 1, wherein the beam reflected back from the proximal end portion of the optical element is that of the polarization state that corresponds to the full transmission axis of the polarizing beam splitter.

3. The method of claim 1, wherein the beam reflected back from the distal end portion of the optical element is at least partially S-polarized.

4. The method of claim 1, further comprising the step of providing a calibration medium, the calibration medium being situated on the distal end portion of the optical element.

5. The method of claim 1, further comprising the step of storing the energy level detected by one or more of the first and second detectors.

6. The method of claim 1, further comprising a third detector, the third detector being operatively associated with the at least one non-polarizing beam splitter and positioned to receive a portion of the beam of coherent light energy to provide a normalization factor measurement.

7. The method of claim 1, wherein the at least one non-polarizing beam splitter and the polarizing beam splitter are arranged in a tandem manner and the beam of coherent light energy passed first through the non-polarizing beam splitter and then the polarizing beam splitter before being transmitted to the optical element.

8. The method of claim 7, further comprising a minor positioned after the polarizing beam splitter to fold the light path of the coherent light beam towards the proximal end portion of the optical element.

9. The method of claim 8, further comprising a light filter element interposed between the polarized beam splitter and the minor.

10. Apparatus for determining the optical quality of an optical element, the optical element having proximal and distal end portions, comprising:
   at least one non-polarizing beam splitter;
   at least one polarizing beam splitter;
   at least a first detector operatively associated with the at least one non-polarizing beam splitter;
   at least a second detector operatively associated with the at least one polarizing beam splitter;
   a mechanism to transmit at least one beam of coherent light energy through the at least one non-polarizing beam splitter and through the at least one polarizing beam splitter, the beam being directed to the proximal and distal end portions of the optical element;
   wherein the beam of coherent light energy that is reflected from the proximal end portion of the optical element is directed back through the at least one polarizing and the at least one non-polarizing beam splitters to the first detector;
   wherein the beam that is reflected from the distal end portion of the optical element is directed back through the at least one polarized beam splitter to the second detector; and,
   wherein the energy level detected by the first and the second detectors provides a measure of optical quality of the optical element.

11. The apparatus of claim 10, wherein the beam reflected back from the proximal end portion of the optical element is that of the polarization state that corresponds to the full transmission axis of the polarized beam splitter.

12. The apparatus of claim 10, wherein the beam reflected back from the distal end portion of the optical element is at least partially S-polarized.

13. The apparatus of claim 10, further comprising a calibration medium, the calibration medium being placed on the distal end portion of the optical element.

14. The apparatus of claim 10, further comprising a storage device for storing the energy level detected by one or more of the detectors.

15. The apparatus of claim 10, further comprising a third detector, the third detector being operatively associated with the at least one non-polarizing beam splitter and positioned to receive a portion of the beam of coherent light energy to provide a normalization factor measurement.

16. The apparatus of claim 10, wherein the at least one non-polarizing beam splitter and the polarizing beam splitter are arranged in a tandem manner and the beam of coherent light energy passed first through the non-polarizing beam splitter and then the polarizing beam splitter before being transmitted to the optical element.

17. The apparatus of claim 16, further comprising a mirror positioned after the polarizing beam splitter to fold the light path of the coherent light beam towards the proximal end portion of the optical element.

18. The apparatus of claim 17, further comprising a light filter element interposed between the polarized beam splitter and the minor.

* * * * *